United States Patent [19]

Lewis et al.

[11] Patent Number: 4,873,390

[45] Date of Patent: Oct. 10, 1989

[54] CHEMICAL CONVERSION PROCESS

[75] Inventors: Jeffrey M. O. Lewis, Charleston; Joe B. Price, Hamlin, both of W. Va.

[73] Assignee: UOP, Des Plaines, Ill.

[21] Appl. No.: 70,575

[22] Filed: Jul. 7, 1987

[51] Int. Cl.$^4$ ............................ C07C 1/00; C07C 1/24
[52] U.S. Cl. .................................. 585/638; 585/639; 585/640; 502/38
[58] Field of Search ............... 208/120, 158, 160, 161, 208/114; 585/639, 640, 638; 502/38

[56] References Cited

U.S. PATENT DOCUMENTS

| | | | |
|---|---|---|---|
| 4,338,475 | 7/1982 | Pennington et al. | 585/640 |
| 4,482,744 | 11/1984 | Audeh | 585/639 |
| 4,499,327 | 2/1985 | Kaiser | 502/60 |
| 4,513,160 | 4/1985 | Avidan et al. | 208/158 |
| 4,547,616 | 10/1985 | Avidan et al. | 585/639 |
| 4,556,540 | 12/1985 | Benslay | 208/161 |
| 4,584,090 | 4/1986 | Farnsworth | 208/114 |
| 4,606,810 | 8/1986 | Krambeck | 208/155 |
| 4,612,406 | 9/1986 | Long et al. | 585/640 |
| 4,627,911 | 12/1986 | Chen et al. | 585/640 |
| 4,666,875 | 5/1987 | Pellet et al. | 502/65 |
| 4,677,243 | 6/1987 | Kaiser | 585/639 |
| 4,752,651 | 6/1988 | Kaiser | 585/638 |
| 4,777,156 | 10/1988 | Forbus et al. | 585/640 |
| 4,814,541 | 3/1989 | Lewis | 585/640 |

Primary Examiner—Anthony Mc Farlane
Attorney, Agent, or Firm—Thomas K. McBride; John G. Tolomei

[57] ABSTRACT

A process for catalytically converting a feedstock into a product which comprises:

(a) contacting the feedstock with a solid composition comprising an effective amount to promote the chemical conversion of small pore crystalline microporous three dimensional solid catalyst at conditions effective to convert the feedstock into the product and to form carbonaceous deposit material on the solid composition;

(b) contacting the carbonaceous deposit material-containing solid composition with regeneration medium at conditions effective to remove only a portion of the carbonaceous deposit material from the solid composition; and (c) repeating step (a) using as at least a portion of the solid composition previously subjected to step (b).

16 Claims, No Drawings

CHEMICAL CONVERSION PROCESS

FIELD OF THE INVENTION

This invention relates to a chemical conversion process employing a catalyst. More particularly, the invention relates to such a chemical conversion process employing certain defined catalysts which provides outstanding results.

BACKGROUND OF THE INVENTION

Chemical conversions employing solid catalysts are often conducted using a fixed ebullating, moving or fluidized bed of catalyst-containing particles. Also, catalyst/liquid slurry reaction systems may be utilized. See commonly assigned U.S. patent applications Ser. Nos. 070,579, 070,574 and 070,578, each filed Jul. 7, 1987, respectively. Each of these applications is incorporated in its entirety by reference herein.

Catalysts comprising one or more crystalline microporus three dimensional solid materials or CMSMs, i.e., catalysts which promote chemical reactions of molecules having selected sizes, shapes and/or transition states, include naturally occurring mineral molecular sieves and synthetic molecular sieves, together referred to as "molecular sieves," and layered clays.

Catalyst-containing particles often include one or more matrix materials, such as binders and fillers, to provide a desired property or properties to the particles. These matrix materials often promote undesirable chemical reactions or otherwise detrimentally affect the catalytic performance of the catalyst. These matrix materials may be particularly troublesome when used in conjunction with relatively highly selective catalysts having sieving properties.

Methanol is readily producible from coal and other raw materials by the use of well-known commercial processes. For example, synthesis gas can be obtained by the combustion of any carbonaceous material including coal or any organic material such as hydrocarbons, carbohydrates and the like. The synthesis gas can be manufactured into methanol by a well known heterogeneous catalytic reaction.

"Hydrocarbons from Methanol" by Clarence D. Chang, published by Marcel Dekker, Inc. N.Y. (1983) presents a survey and summary of the technology described by its title. Chang discussed methanol to olefin conversion in the presence of molecular sieves at pages 21–26. The examples given by Chang as suitable molecular sieves for converting methanol to olefins are chabazite, erionite, and synthetic zeolite ZK-5. The channel dimensions are calculated from a theoretical model.

U.S. Pat. Nos. 4,238,631; 4,328,384; and 4,423,274 disclose processes for converting methanol to olefin-enriched or gasoline boiling range hydrocarbons in the presence of fluid catalyst particles having a zeolite with a pore opening of at least 5 angstroms. These zeolites are distinguished by virtue of having an effective pore size intermediate between the small pore Linde A and the large pore Linde X, i.e., the pore windows of the structure are the size which would be provided by 10 member rings of silicon atoms interconnected by oxygen atoms. These zeolites, which include ZSM-5, ZSM-11, ZSM-12, ZSM-23, ZSM-35, ZSM-38 and ZSM-48. These patents disclose that such intermediate pore size zeolites can be utilized by maintaining a high coke level on the catalyst, in the range of 5 to 20 weight %, to preferentially produce olefins. U.S. Pat. No. 4,079,095 discloses a process for making light olefins from methanol using ZSM-34, which is a zeolite having a pore size somewhat smaller than the zeolites described in the other patents noted in this paragraph. However, no olefin selectivity advantage for maintaining a high coke level was disclosed when using the smaller pore ZSM-34 zeolite.

Among the CMSMs that can be used to promote converting methanol to olefins are non-zeolitic molecular sieves or NZMSs such as aluminophosphate or ALPOs, in particular silicoaluminophosphates or SAPOs disclosed in U.S. Pat. No. 4,440,871. U.S. Pat. No. 4,499,327 issued Feb. 12, 1985, discloses processes for catalytically converting methanol to light olefins using SAPOs at effective process conditions. This U.S. Patent is incorporated in its entirety by reference herein.

SUMMARY OF THE INVENTION

A process for catalytically converting a feedstock into a product has been discovered. In one broad aspect, the process comprises: (a) contacting the feedstock with a solid composition comprising an effective amount to promote the desired chemical conversion of a crystalline microporous three dimensional solid catalyst, a CMSC, having small pores (i.e., a small pore CMSC) at conditions effective to convert the feedstock into the product and to form carbonaceous deposit material on the solid composition; (b) contacting the deposit material-containing solid composition with regeneration medium at conditions effective to remove only a portion of the deposit material; and (c) repeating step (a) using as at least a portion of the solid composition the solid composition previously subjected to step (b). The present process is particularly useful where the feedstock contains 1 to about 10, more particularly 1 to about 4, carbon atoms per molecule, still more particularly methanol, and the desired product contains about 2 to about 10 carbon atoms per molecule, more particularly olefins selected from the group consisting of ethylene, propylene, butylenes and mixtures thereof.

DISCUSSION OF THE INVENTION

The present catalytic conversion process provides substantial advantages. For example, the present partially regenerated solid composition, produced in step (b), provides improved catalytic performance, e.g., improved selectivity to the desired product or products, relative to the solid composition containing less of the carbonaceous deposit material, e.g., the solid composition subjected to the action of regeneration medium to provide a solid composition substantially free of such carbonaceous deposit material. This is particularly surprising in view of previous work, discussed above, which at least implies that catalysts comprising small pore molecular sieves are not benefited by the initial presence of carbonaceous deposit material. Notwithstanding this previous work, a substantial benefit has been found using such relatively small pore CMSCs which can lead to improved overall process efficiency, e.g., reduced feedstock and operating costs, and increased yields of desired product or products. The level of catalytic activity can be controlled to produce substantially improved results using such relatively small pore CMSCs.

Step (a) of the present process results in the formation of carbonaceous deposit material on the solid composition, e.g., solid particles. Such carbonaceous deposit material is coke-like (and is often referred to as coke), and often contains a substantially reduced amount of hydrogen relative to the feedstock. These deposits result in the CMSC losing at least a portion of at least one desirable property, e.g., catalytic activity. The catalyst is contacted with regeneration medium in step (b) to remove only a portion of the carbonaceous deposit material from the solid composition or particles. For example, a portion of the carbonaceous deposit material is removed by oxidation in an oxygen-containing gaseous atmosphere.

Step (b) is controlled so that only a portion of the carbonaceous deposit material is removed from the solid composition or the solid particles. Preferably, step (b) is controlled so that less than about 90%, more preferably less than about 70% and still more preferably less than about 60%, of the carbonaceous deposit material is removed from the solid composition. The carbonaceous deposit material-containing solid composition from step (a) is preferably contacted with regeneration medium in step (b) so that substantially the same relative amount of carbonaceous deposit material is removed from each component, e.g., catalyst and matrix materials, of the solid composition. Without limiting the present invention to any specific theory or mechanism of operation, the carbonaceous deposit material on the solid composition leaving step (b) may reduce the catalytic activity of the matrix materials which is often relatively non-selective for the desired product.

In one embodiment, it is preferred that the rate of carbonaceous deposit material removal in step (b) be reduced relative to the rate of removal when substantially all the carbonaceous material is to be removed from the solid composition. Such reduced removal rate may provide improved uniformity of carbonaceous deposit material removal. One approach to achieving this reduced removal rate is to reduce the amount of regeneration medium available at any one time. For example, if oxygen is the regeneration medium, the average partial pressure of oxygen contacting the solid composition during step (b) is preferably reduced relative to the average oxygen partial pressure required to remove substantially all of the carbonaceous deposit material from the solid composition with all other conditions, e.g., step (b) conditions, being equal. Preferably, the average oxygen partial pressure in step (b) is less than about 90%, more preferably less than about 70% and still more preferably less than about 60% of the average oxygen partial pressure required to substantially completely remove the carbonaceous deposit material from the same mass of solid composition (having the same chemical and structural make-up) at the same conditions, e.g., of time, temperature, pressure and the like.

Although only a portion of the carbonaceous deposit material is removed from the solid composition during step (b), that portion is preferably substantial enough to at least maintain, more preferably increase, the catalytic activity of the solid composition after step (b). In one embodiment, the solid composition after being subjected to step (b) preferably contains about 2% to about 30%, more preferably about 3% to about 25% and still more preferably about 4% to about 20%, by weight of carbonaceous deposit material.

As noted above, the presently useful CMSCs have relatively small pores. The presently useful small pore CMSCs are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the CMSC and adsorption of the adsorbate is over three percent by weight of the adsorbate based on the weight of the CMSC. Certain of the CMSCs useful in the present invention have pores with an average effective diameter of less than 5 angstroms. The average effective diameter of the pores of the presently useful catalysts is determined by measurements described in "Zeolite Molecular Sieves" by Donald W. Breck, published by John Wiley & Sons, New York, 1974. Preferably, the small pore CMSCs has a substantially uniform pore structure, e.g., substantially uniformly sized and shaped pores. Suitable CMSCs may be chosen from among layered clays, zeolitic molecular sieves and non-zeolitic molecular sieves or NZMSs.

The presently useful NZMSs include certain molecular sieves which have the proper effective pore size and are embraced by an empirical chemical composition, on an anhydrous basis, expressed by the formula:

$$mR: (Q_wAl_xP_yS_{nz})O_2 \qquad (I)$$

where "Q" represents at least one element present as a framework oxide unit "QO$_2^n$" with charge "n" where"" may be $-3, -2, -1, 0$ or $+1$; "R" represents at least one organic templating agent present on the intracrystalline pore system; "m" represents the molar amount of "R" present per mole of $(Q_wAl_xP_ySi_z)O_2$ and has a value from zero to about 0.3; and "w", "x", "y" and "z" represent the mole fractions of $QO_2^n$, $AlO_2^-$; $PO_2^+$, $SiO_2$, respectively, present as framework oxide units. "Q" is characterized as an element having a mean "T-O" distance in tetrahedral oxide structures between about 1.51 Å and about 2.06 Å. "Q" has a cation electronegativity between about 125 kcal/g-atom to about 310 kcal/gm-atom and "Q" is capable of forming stable Q-O-P, Q-O-Al or Q-O-Q bonds in crystalline three dimensional oxide structures having a "Q-O" bond dissociation energy greater than about 59 kcal/g-atom at 298° K[1]; and "w", "x", "y" and "z" represent the mole fractions of "Q", aluminum, phosphorus and silicon, respectively, present as framework oxides said mole fractions being within the limiting compositional values or points as follows:
w is equal to 0 to 99 mole percent;
y is equal to 1 to 99 mole percent;
x is equal to 1 to 99 mole percent; and
z is equal to 0 to 99 mole percent.

[1] See the discussion at pages 8a, 8b and 8c of EPC Publication 0 159 624, published Oct. 30, 1985, about the characterization of "EL" and "M". Such are equivalent to Q as used herein.

The "Q" of the "QAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. Combinations of the elements are contemplated as representing Q, and to the extent such combinations are present in the structure of a QAPSO they may be present in molar fractions of the Q component in the range of 1 to 99 percent thereof. It should be noted that formula (I) contemplates the non-existence of Q and Si. In such case, the operative structure is that of aluminophosphate or AlPO$_4$. Where z has a positive value, then the operative structure is that of silicoaluminophosphate or SAPO. Thus, the term QAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various compositions and structures described in the patents and patent applications set forth in Table A, which follows, and ty Flanigen et al., in the paper entitled, "Aluminophosphate Molecular Sieves and the Periodic Table," published in the "New Developments and Zeolite Science Technology" Proceedings of the 7th International Zeolite Conference, edited by Y. Murakami, A. Sijima and J. W. Ward, pages 103–112 (1986):

TABLE A

| Patent or Pat. Applic. No. | Subject Matter of Patent or Patent Application |
|---|---|
| U.S. Pat. No. 4,567,029 | MAPO's are crystalline metal aluminophosphates having a three-dimensional microporous framework structure of MO$_2^{-2}$, AlO$_2^-$ and PO$_2^+$ tetrahedral units and having an empirical chemical composition on an anhydrous basis expressed by the formula mR:(M$_x$Al$_y$P$_z$)O$_2$; where R represents at least one organic templating agent present in the intracrystalline pore system; m has a typical value of from 0 to 0.3 and represents the moles of R present per mole of (M$_x$Al$_y$P$_z$)O$_2$; M represents magnesium, manganese, zinc or cobalt, x, y and z represent the mole fractions of M, aluminum and phosphorus, respectively, present as tetrahedral oxides. The fractions are such that they are within a tetragonal compositional area defined by points ABC and D of FIG. 1 of the drawings of the patent. This patent, at column 6, describes the use of aluminophosphates as a source of phosphorus (lines 26-28) and as a source of aluminum (lines 38-40), and the use of seed crystals to aid in the crystallization of the desired molecular sieve (lines 59-63). Example 85 depicts the use of MAPO-36 as a seed for making MnAPO-36. The chemical composition of the MnAPO-36 fails to reveal the presence of any magnesium. |
| U.S. Pat. No. 4,440,871 | SAPO molecular sieves are a general class of microporous crystalilne silicoaluminophosphates. The pores have a nominal diameter of greater than about 3 Å. The "essentially empirical composition" is mR:(Si$_x$Al$_y$P$_z$)O$_2$, where R represents at least one organic templating agent present in the intracrystalline pore system; m has a typical value of from 0 to 0.3 and represents the moles of R present per mole of (Si$_x$Al$_y$P$_z$)O$_2$; x, y and z represent the mole fractions of silicon, aluminum and phosphorus, respectively, present as tetrahedral oxides. The fractions are such that they are within a pentagonal compositional area defined by points A, B, C, D and E of the ternary diagram of FIG. 1 and preferably within the pentagonal compositional area defined by points a, b, c, d and e of FIG. 2, of the drawings of the patent. The SAPO molecular sieves have a characteristic x-ray powder diffraction pattern which contains at least the d-spacings set forth in any one of Tables I, III, V, VII, IX, XI, XIII, XV, XVII, XIX, XXI, XXIII or XXV of the patent. Further, the as-synthesized crystalline silicoaluminophosphates of the patent may be calcined at a temperature sufficiently high to remove at least some of any organic templating agent present in the intracrystalline pore system as a result of such synthesis. The silicoaluminophosphates are generally referred to therein as "SAPO", as a class, or as "SAPO-n" wherein "n" is an integer denoting a particular SAPO as its preparation is reported in the patent. The U.S. patent speaks at column 8, lines 12-16 of employing seed crystals to generate SAPO species. That technique is described in examples 22, 51 and 53. |
| U.S. Ser. No. 600,312 filed April 13, 1984, commonly assigned, EPC Public. 0 159 624, published October 30, 1985 | ELAPSO molecular sieves have the units ELO$_2^n$, AlO$_2^-$, PO$_2^+$, SiO$_2$ in the framework structure and have an empirical chemical composition on an anhydrous basis expressed by the formula mR:(EL$_w$Al$_x$P$_y$Si$_z$)O$_2$ where "EL" represents at least one element present as a framework oxide unit "ELO$_2^n$" with charge "n" where "n" may be −3, −2, −1, 0 or +1; "R" represents at least one organic templating agent present on the intracrystalline pore system; "m" represents the molar amount of "R" present per mole of (EL$_w$Al$_x$P$_y$Si$_z$)O$_2$ and has a value from zero to about 0.3; and "w", "x", "y" and "z" represent the mole fractions of ELO$_2^n$, AlO$_2^-$, PO$_2^+$, SiO$_2$, respectively, present as framework oxide units. "EL" is characterized as an element having (a) a mean "T—O" distance in tetrahedral oxide structures between about 1.51 Å and about 2.06 Å, (b) a cation electronegativity between about 125 kcal/g-atom to about 310 kcal/gm-atom and (c) a capability of forming stable M—O—P, M—O—Al or M—O—M bonds in crystalline three dimensional oxide structures having a "M-O" bond dissociation energy greater than about 59 kcal/g-atom at 298° K. "w", "x", "y" and "z" represent the mole fractions of "EL", aluminum, phosphorus and silicon, respectively, present as framework oxides. The mole fractions are within the limiting compositional values or points as follows: |

| | | Mole Fraction | |
|---|---|---|---|
| Point | x | y | (z + w) |
| A | 0.60 | 0.39−(0.01 p) | 0.01(p + 1) |
| B | 0.39−(0.01 p) | 0.60 | 0.01(P + 1) |
| C | 0.01 | 0.60 | 0.39 |
| D | 0.01 | 0.01 | 0.98 |
| E | 0.60 | 0.01 | 0.39 | where "p" is an integer corresponding to the number of elements which "EL" represents in the (EL$_w$Al$_x$P$_y$Si$_z$)O$_2$ composition. The "EL" of the "ELAPSO" molecular sieves may be defined as representing at least one element capable of forming a TABLE A-continued

| Patent or Pat. Applic. No. | Subject Matter of Patent or Patent Application |
|---|---|
| | framework tetrahedral oxide and is preferably selected from the group consisting of arsenic, beryllium, boron, chromium, cobalt, gallium, germanium, iron, lithium, magnesium, manganese, titanium and zinc and "w", "x", "y" and "z" represent the mole fractions of "EL", aluminum, phosphorus and silicon, respectively, present at tetrahedral oxides in which the mole fractions are within the limiting compositional values or points as follows: |

| Point | Mole Fraction | | |
|---|---|---|---|
| | x | y | (z + w) |
| a | 0.60 | 0.39−(0.01 p) | 0.01(p + 1) |
| b | 0.39−(0.01 p) | 0.60 | 0.01(p + 1) |
| c | 0.10 | 0.55 | 0.35 |
| d | 0.55 | 0.10 | 0.35 |

| Patent or Pat. Applic. No. | Subject Matter of Patent or Patent Application |
|---|---|
| | where "p" is as above defined. The EP publication at page 16 discloses the use of crystalline and amorphous aluminophosphate as a source of phosphorus and aluminum and at page 17 describes seeding the reaction mixure. Examples 11A, 12A, 93A-103A, 5B, 6B, 55B, 58B, 59B, 50D-56D, 59D-62D and 12F-15F depict the use of seed crystals. |
| U.S. Pat. No. 4,500,651, patented Feb. 19, 1985 | TAPO molecular sieves comprise three-dimensional microporous crystalline framework structures of $[TiO_2]$, $[AlO_2]$ and $[PO_2]$ tetrahedral units which have a unit empirical formula on an anhydrous basis of: $mR:(Ti_xAl_yP_z)O_2$ (1) wherein "R" represents at least one organic templating agent present in the intracrystalline pore system; "m" represents the moles of "R" present per mole of $(Ti_xAl_yP_z)O_2$ and has a value of from zero to 5.0, the maximum value in each case depending upon the molecular dimensions of the templating agent and the available void volume of the pore system of the particular titanium molecular sieve; "x", "y" and "z" represent the mole fractions of titanium, aluminum and phosphorus, respectively, present as tetrahedral oxides, representing the following values for "x", "y" and "z": |

| Point | Mole Fraction | | |
|---|---|---|---|
| | x | y | (z + w) |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.0001 | 0.70 | 0.299 |

The parameter "x", "y" and "z" are preferably within the following values for "x", "y" and "z":

| Point | Mole Fraction | | |
|---|---|---|---|
| | x | y | (z + w) |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The TAPO molecular sieves are generally further characterized by an intracrystalline adsorption capacity for water at 4.6 torr and about 24° C., of about 3.0 weight percent. The adsorption of water has been observed to be completely reversible while retaining the same essential framework topology in both the hydrated and dehydrated state. The U.S. Patent at column 8, lines 65-68, and column 9, lines 15-18, discusses the use of crystalline amorphous aluminophosphate as a source of phosphorus and aluminum. At column 6, lines 1-5, seeding is described as facilitating the crystallization procedure. Comparative example 44 describes a composition of amorphous $TiO_2$ and 95 wt. % $AlPO_418$ without an indication of how the composition was prepared

| Patent or Pat. Applic. No. | Subject Matter of Patent or Patent Application |
|---|---|
| U.S. Ser. No. 600,179, filed Apr. 13, 1984, EPC Publication 0 161 488, published Nov. 21, 1985 | The TiAPSO molecular sieves have three-dimensional microporous framework structures of $TiO_2$, $AlO_2^-$, $PO_2^+$ and $SiO_2$ tetrahedral oxide units having an empirical chemical composition on an anhydrous basis expressed by the formula: $mR:(Ti_wAl_xP_ySi_z)O_2$ wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined in respect to the ternary diagram of FIG. 1 of the applications as being within the following limiting compositional values or points: |

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d of the ternary diagram of FIG. 2 of the applications, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

| Patent or Pat. Applic. No. | Subject Matter of Patent or Patent Application |
|---|---|
| | The publication, at page 13, describes the use of crystalline or amorphous aluminophosphate as a source of phosphorus and aluminum and, at page 14, points out that seeding the reaction mixture facilitates the crystallization procedure. |
| U.S. Pat. No. 4,554,143, patented Nov. 19, 1985 | Ferroaluminophosphates (FAPO's) are disclosed in U.S. Pat. No. 4,554,143, incorporated herein by reference, and have a three-dimensional microporous crystal framework structure of $AlO_2$, $FeO_2$ and $PO_2$ tetrahedral units and have an essential empirical chemical composition, on an anhydrous basis, of: $mR:(Fe_xAl_yP_z)O_2$ wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y" and "z" represent the mole fractions of iron, aluminum and phosphorus, respectively, present as tetrahedral oxides, representing the following values for "x", "y" and "z": |

TABLE A-continued

| Patent or Pat. Applic. No. | Subject Matter of Patent or Patent Application |
|---|---|

| | | Mole Fraction | |
|---|---|---|---|
| Point | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values of "x", "y" and "z":

| | | Mole Fraction | |
|---|---|---|---|
| Point | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units can be in either the ferric or ferrous valence state, depending largely upon the source of the iron in the synthesis gel. Thus, a $FeO_2$ tetrahedron in the structure can have a net charge of either −1 or −2.
The patent indicates at column 5, lines 43–45 and 54–56, that crystalline amorphous aluminophosphate may be used as a source of phosphorus and aluminum and at column 6, lines 1–5, describes seeding of the reaction mixture as facilitating the crystallization procedure.

| U.S. Application S.N. 600,173 filed April 13, 1984, EPC Publication 0 161 491, published Nov. 21, 1985 | The FeAPSO molecular sieves have a three-dimensional microporous crystal framework structures of $FeO_2^{-2}$ (and/or $FeO_2$), $AlO_2$, $PO_2$ and $SiO_2$ tetrahedral oxide units and having a unit empirical formula, on an anhydrous basis, of: $mR:(Fe_wAl_xP_ySi_z)O_2$ (1) wherein "R" represents at least one organic templating agent present in the intracrystalline pore system; "m" represents the moles of "R" present per mole of $(Fe_wAl_xP_ySi_z)O_2$ and has a value of from zero to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows: |
|---|---|

| | | Mole Fraction | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| | | Mole Fraction | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication, at page 12, describes the use of seeding the reaction mixture to facilitate the crystallization procedure. At page 18, the publication describes the use of crystalline amorphous aluminophosphates as a source of phosphorus and aluminum in making the molecular sieve.

| U.S. Ser. No. 600,170, EPC Publication 0 158 975, published Oct. 23, 1985 | The ZnAPSO molecular sieves of U.S. Ser. No. 600,170, filed April 13, 1984 comprise framework structures of $ZnO_2^{-2}$, $AlO_2^-$, $PO_2^+$ and $SiO_2$ tetrahedral units havings an empirical chemical composition on an anhydrous basis expressed by the formula: $mR:(Zn_wAl_xP_ySi_z)O_2$ wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows: |
|---|---|

| | | Mole Fraction | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| | | Mole Fraction | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication at page 13 discloses that crystalline or amorphous aluminophosphate may be used as a source of phosphorus or aluminum and at page 14 indicates that seeding of the reaction mixture with said crystals facilitates the crystallization procedure. Examples 12–15 are stated to employ the seeding procedure.

| U.S. Application S.N. 600,180, filed April 13, 1984, EPC Publication 0 158 348, published Oct. 16, 1985 | The MgAPSO molecular sieves have three-dimensional microporous framework structures of $MgO_2^{-2}$, $AlO_2^-$, $PO_2^+$ and $SiO_2$ tetrahedral oxide units and have an empirical chemical composition on an anhydrous basis expressed by the formula: $mR:(Mg_wAl_xP_ySi_z)O_2$ wherein "R" represents at least one organic templating agent present in the intracrystalline pore system; "m" represents the molar amount of "R" present per mole of $(Mg_wAl_xP_ySi_z)O_2$ and has a value from zero to about 0.3; and "w", "x", "y" and "z" represent the mole fractions of magnesium, aluminum, phosphorus and silicon, respectively, present as tetrahedral oxides and each preferably as a value of at least 0.01. The mole fractions "w", "x", "y" and "z" are generally defined as being within the limiting compositional values or points as follows: |
|---|---|

| | | Mole Fraction | |
|---|---|---|---|
| Point | x | y | (z + w) |
| A | 0.60 | 0.38 | 0.02 |
| B | 0.39 | 0.59 | 0.02 |

TABLE A-continued

| Patent or Pat. Applic. No. | Subject Matter of Patent or Patent Application | | | |
|---|---|---|---|---|
| | C | 0.01 | 0.60 | 0.39 |
| | D | 0.01 | 0.01 | 0.98 |
| | E | 0.60 | 0.01 | 0.39 |

In a preferred subclass of the MgAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication depicts seeding to generate product at page 14 and in examples 5, 6, 55, 58 and 59.

| Patent or Pat. Applic. No. | Subject Matter of Patent or Patent Application |
|---|---|
| U.S. Application Ser. No. 600,175, filed April 4, 1984 EPC Publication 0 161 490, published Nov. 11, 1985 | The MnAPSO molecular sieves of U.S. Ser. No. 600,175 filed April 13, 1984 have a framework structure of $MnO_2^2$, $AlO_2$, $PO_2$, and $SiO_2$ tetrahedral units having an empirical chemical composition on an anhydrous basis expressed by the formula: $mR:(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows |

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication at page 13 describes the use of crystal or amorphous aluminophosphate as a source of phosphorus or aluminum, and at page 14 characterizes the use of said crystals to facilitate the crystallization procedure. Examples 54–56 and 59–62 state said crystals were used in the manufacture of the MnAPSO products.

| Patent or Pat. Applic. No. | Subject Matter of Patent or Patent Application |
|---|---|
| U.S. Application Ser. No. 600,174, filed April 13, 1984, EPC Publication 0 161 489 published Nov. 21, 1985 | The CoAPSO molecular sieves of U.S. Ser. No. 600,174, filed April 13, 1984 have three-dimensional microporous framework structures of $CoO_2^2$, $AlO_2$, $PO_2$ and $SiO_2$ tetrahedral units and have an empirical chemical composition on an anhydrous basis expressed by the formula: $mR:(Co_wAl_xP_ySi_z)O_2$ wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represents the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows: |

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values of "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication at page 13 depicts the use of crystalline amorphous aluminophosphate as a source of phosphorus and aluminum and at page 14 states that seeding the reaction mixture facilitates the crystallization procedure. Examples 11, 12, 13, 93 and 97–103 depict the use of seed crystals.

| Patent or Pat. Applic. No. | Subject Matter of Patent or Patent Application |
|---|---|
| U.S. 599,771 599,776 599,807, 599,809, 599,811 599,812 599,813 600,166 600,171 each filed April 13, 1984, EPC Publication 0 158 976, published Oct. 23, 1985 | MeAPO molecular sieves are crystalline microporous aluminophosphates in which the substituent metal is one of a mixture of two or more divalent metals of the group magnesium manganese, zinc and cobalt and are disclosed in U.S. Pat. No. 4,567,028. Members of this novel class of compositions have a three-dimensional microporous crystal framework structure of $MO_2^2$, $AlO_2$ and $PO_2$ tetrahedral units and have the essentially empirical chemical composition, on an anhydrous basis, of: $mR:(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y" and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y" and "z": |

| | Mole Fraction | | |
|---|---|---|---|
| Point | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are

TABLE A-continued

| Patent or Pat. Applic. No. | Subject Matter of Patent or Patent Application |
|---|---|
| | representing the following values for "x", "y" and "z": |

| Point | Mole Fraction | | |
|---|---|---|---|
| | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

| Patent or Pat. Applic. No. | Subject Matter of Patent or Patent Application |
|---|---|
| | The as-synthesized compositions are capable of withstanding 350° C. calcination in air for extended periods, i.e., at least 2 hours, without becoming amorphous. The EP publication at pages 14 and 15 depicts the use of crystalline and amorphous aluminophosphate as a source of phosphorus and aluminum and at page 15 states that seeding the reaction mixture facilitates the crystallization procedure. Example 8 discloses seeding of crystals. |
| EPC Applic. 85104386.9, filed April 11, 1985 (EPC Publication No. 0158976, published October 13, 1985) and EPC Applic. 85104388.5, filed April 11, 1985 (EPC Publication No. 158348, published October 16, 1985) | "ELAPO" molecular sieves are a class of crystalline molecular sieves in which at least one element capable of forming a three-dimensional microporous framework form crystal framework structures of $AlO_2$, $PO_2$ and $MO_2$ tetrahedral oxide units wherein "$MO_2$" represents at least one different element (other than Al or P) present as tetrahedral oxide units "$MO_2$" with charge "n" where "n" may be −3, −2, −1, 0 or +1. The members of this novel class of molecular sieve compositions have crystal framework structures of $AlO_2$, $PO_2$ and $MO_2$ have an empirical chemical composition on an anhydrous basis expressed by the formula. $mR:(M_xAl_yP_z)O_2$ wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different elements ($M_1$) such that the molecular sieves contain at least one framework tetrahedral units in addition to $AlO_2$ and $PO_2$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc. The ELAPO molecular sieves are generally referred to herein by the acronym or "ELAPO" to designate element(s) "M" in a framework of $AlO_2$, $PO_2$ and $MO_2$ tetrahedral oxide units. Actual class members will be identified by replacing the "EL" of the acronym with the elements present as $MO_2$ tetrahedral units. When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed. |
| | The ELAPO molecular sieves have crystalline three-dimensional microporous framework structures of $AlO_2$, $PO_2$ and $MO_2$ tetrahedral units and have an empirical chemical composition on an anhydrous basis expressed by the formula: $mR:(M_xAl_yP_z)O_2$; wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc. The relative amounts of element(s) "M", aluminum and phosphorus are expressed by the empirical chemical formula (anhydrous): $mR:(M_xAl_yP_z)O_2$ where "x", "y" and "z" represent the mole fractions of said "M", aluminum and phosphorus The individual mole fractions of each "M" (of when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x" hereinafter, where "$x_1$" + "$x_2$" + "$x_3$" ... = "x" and where $x_1$, $x_2$, $x_3$, etc. are each at least 0.01. The ELAPO molecular sieves have crystalline three-dimensional microporous framework structures of $MO_2$, $AlO_2$ and $PO_2$ tetrahedral units having an empirical chemical composition on an anhydrous basis expressed by the formula: $mR:(M_xAl_yP_z)O_2$ wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z": |

| Point | Mole Fraction | | |
|---|---|---|---|
| | x | y | (z + w) |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub-class of the ELAPOs of this invention, the values of "x", "y" and "z" in the formula above are within the following values for "x", "y" and "z":

| Point | Mole Fraction | | |
|---|---|---|---|
| | x | y | (z + w) |
| a | 0.02 | 0.60 | 0.39 |
| b | 0.02 | 0.38 | 0.60 |

TABLE A-continued

| Patent or Pat. Applic. No. | Subject Matter of Patent or Patent Application | | |
|---|---|---|---|
| | c | 0.39 | 0.01 | 0.60 |
| | d | 0.60 | 0.01 | 0.39 |
| | e | 0.60 | 0.39 | 0.01 |
| | f | 0.39 | 0.60 | 0.01 |
| U.S. Pat. No. 4,310,440 | ALPO's are the basic and simplest of the crystalline aluminophosphates. They each having a framework structure whose chemical composition expressed in terms of mole ratios of oxides is: $Al_2O_3:1.0 \pm 0.2P_2O_5$: each of said framework structures being microporous in which the pores are uniform and have nominal diameters within the range of about 3 to about 10Å, an intracrystalline adsorption capacity for water at 4.6 torr and 24° C. of at least 3.5 weight percent, the adsorption and desorption of water being completely reversible while retaining the same essential framework topology in both the hydrated and dehydrated state. | | |
| U.S. Pat. Applications 600,168, 600,181, 600,182, 600,183, European Patent Publ. 0 158 350, publ. Oct. 16, 1985 | SENAPSO are quinary and senary molecular sieves that have framework structures of at least two elements having tetrahedral oxide units "$MO_2^{n}$" and having $AlO_2^-$, $PO_2^+$ $SiO_2$ tetrahedral oxide units, where "n" is $-3, -2, -1, 0$ or $+1$, and have an empirical chemical composition on an anhydrous basis expressed by the formula: $mR:(M_wAl_xP_ySi_z)O_2$ wherein "R" represents at least one organic templating agent present in the intracrystallinepore system; "m" represents the molar amount of "R" present per mole of $(M_wAl_xP_ySi_z)O_2$ and has a value of from 0 to about 0.3; "M" represents at least two elements selected from the group consisting of arsenic, beryllium, boron, chromium, cobalt, gallium, germanium, iron, lithium, magnesium, manganese, titanium, vanadium, and zinc; "n" is as above defined; and "w", "x", "y" and "z" represent the mole fractions of elements "M", aluminium, phosphorus and silicon, respectively, present as tetrahedral oxides, each having a value of at least 0,01. The publication, at pages 14–15, generally describes seeding reaction mixtures to form the desired product | | |

Zeolitic molecular sieves may be represented by the general formula:

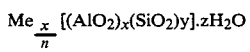

where Me is a metal cation, x/n is the number of exchangeable metal cations of valence n, x is also the number of aluminum ions combined in the form of aluminate, y is the number of silicon atoms and z is the number of water molecules, removal of which produces the characteristic pore or channel system. The ratio z/x is a number from 1 to 5, usually from 1 to 2.

Typical of the zeolitic molecular sieves are chabazite, faujasite levynite, Linde Type A, gismondine, erionite, sodalite, ZSM-34[1] and the like. Other zeolite CMSCs useful in the present invention include boron-treated aluminosilicates, such as described in U.S. Pat. No. 4,613,720. Other NZMSs include the silica molecular sieves, such as silicalite as depicted in U.S. Pat. No. 4,061,724.

[1] See U.S. Pat. No. 4,079,095.

The non-zeolitic molecular sieves or NZMSs are particularly useful in the practice of the present invention. Among the NZMSs, the SAPOs are particularly useful. SAPO-34, which is described in detail in Example 38 of U.S. Pat. No. 4,440,871, are especially preferred catalysts for promoting the reaction of molecules containing 1 to about 4 carbon atoms, e.g., methane, methanol, methyl halide, and the like, to form products containing up to about 6 preferably up to about 4, carbon atoms per molecule, e.g., ethylene, propylene, butylene and the like.

The presently useful CMSCs may be, and preferably are, incorporated into solid particles in which the catalyst is present in an amount effective to promote the desired chemical conversion. In one embodiment, the solid particles comprise a catalytically effective amount of the CMSC and at least one matrix material, preferably selected from the group consisting of binder materials, filler materials and mixtures thereof, to provide a desired property or properties, e.g., desired catalyst dilution, mechanical strength and the like, to the solid particles. Such matrix materials are often to some extent porous in nature and may or may not be effective to promote the desired chemical conversion. The matrix materials may promote conversion of the feedstock during step (a) and often provide reduced selectivity to the desired product or products relative to the sieving catalyst. Filler and binder materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-alumina-zirconias, mixtures of these and the like.

If matrix materials, e.g., binder and/or filler materials, are included in the solid composition, the CMSC preferably comprises about 1% to about 99%, more preferably about 5% to about 90% and still more preferably about 10% to about 80%, by weight of the total solid composition. When the catalyst is used in a slurry system, e.g., with a suspending liquid other than the feedstock or the product, that catalyst preferably is included in solid particles containing no more than about 75%, more preferably no more than about 35%, by weight of other solid material, e.g., matrix material. It is preferred that the solid composition, e.g., particles, include at least one matrix material to provide an effective amount of at least one desired property to the solid composition.

The preparation of solid particles comprising CMSC and matrix materials is conventional and well known in the art and, therefore, need not be discussed in detail here. Certain of such preparation procedures are described in the patents and patent applications previously incorporated by reference herein, as well as in U.S. Pat. Nos. 3,140,253 and RE.27,639. CMSCs which are formed during and/or as part of the methods of manufacturing the solid particles are within the scope of the present invention.

The solid particles including the catalysts may be of any size functionally suitable in the present invention. The catalyst may be employed in a fixed bed, ebullating bed, moving bed or a fluidized bed reaction system, as well as in a catalyst/liquid slurry. The catalyst is preferably utilized in the fluidized state or in a catalyst/liquid slurry reaction system, more preferably in a fluidized state, to provide for ease in controlling the activity of the catalyst, as desired. In order that the catalyst be utilized more effectively, the solid particles are preferably small relative to fixed bed solid particles used to promote similar chemical conversions. More preferably, the solid particles have a maximum transverse dimension, e.g., diameter, in the range of about 1 micron to about 500 microns, still more preferably about 25 microns to about 200 microns.

The catalyst and/or solid particles may be subjected to mechanical size reduction, e.g., grinding, crushing, milling and the like, in order to obtain the desired particle size. However, it is preferred that the solid particles including the catalyst be more smooth, and more preferably also more spherical, relative to solid particles of similar composition obtained by mechanical size reduction. Such particle smoothness and sphericity tends to improve the useful life of the catalyst and, when a slurry system is used, may also allow increased solids loading in the slurry, if desired. One particularly useful processing step to achieve such smoothness and sphericity is to employ spray drying as part of the solid particle manufacturing process to form the solid particles or precursors of the solid particles. An additional advantage of employing such spray drying is that the conditions of such step can be controlled so that the product solid particles are of a desired particle size or size range. The use of spray drying in such catalyst/solid particle manufacturing is conventional and well known, and therefore need not be discussed in detail here.

The amount of solid composition, e.g., solid particles, in the step (a) contacting zone, e.g., the reaction zone, may vary over a wide range depending, for example, on the specific processing application involved. If a solid particles/liquid slurry is employed, relatively high loadings of solid particles in the slurry may be appropriate in order to contact the feedstock and catalyst in a space and time effective manner. On the other hand, excessive solid particle loadings are to be avoided since reduced desired product might result. Preferably, the solid particles comprise about 0.1% to about 50%, more preferably about 0.2% to about 30%, by weight of the slurry.

If a slurry system is employed, it is preferred to use a suspending liquid in the presently useful slurry which is less reactive than the feedstock. That is, the suspending liquid is less likely to chemically react, e.g., by itself or with the feedstock, product and diluent (if any), at the conditions of the feedstock/catalyst contacting step. Thus, the rate of chemical conversion or reaction of the suspending liquid is reduced, preferably substantially reduced, relative to such rate for the feedstock at the conditions of the feedstock/catalyst contacting step. More preferably, the suspending liquid is substantially non-reactive, i.e., does not substantially chemically react or is substantially chemically inert, at the conditions of the present feedstock/catalyst contacting step, particularly with regard to chemical reactions promoted by the presently useful catalyst. The suspending liquid may degrade or deteriorate, e.g., by oxidation, thermal cracking and the like, over a relatively long period of time at contacting conditions, e.g., elevated temperature. Such degradation or deterioration may result in replacing the suspending liquid, but should not be considered in determining whether the liquid is substantially non-reactive. Preferably, the composition of the suspending liquid is chosen so that the size and/or shape of the liquid's molecules are inconsistent with access to the pores of the catalyst. For example, the molecules of the liquid may be too big to enter the pores of the catalyst.

The suspending liquid may be chosen from a wide variety of compositions provided it functions as described herein. The liquid should be stable, i.e., substantially resistant to deterioration or decomposition at the conditions of step (a) which often include elevated temperatures, for example, in excess of about 300° C. In one embodiment, the molecules of the suspending liquid have a kinetic diameter or diameters of a size to substantially prevent such molecules from entering the pores of the sieving catalyst. The liquid may be inorganic or organic. One or more silicones and the like materials may be used as the suspending liquid. Suitable organic liquids preferably include carbon and hydrogen, and more preferably at least one other element, for example, halogen, nitrogen, oxygen, phosphorus, sulfur and mixtures thereof, with liquids comprising carbon, hydrogen and oxygen-containing molecules being particularly useful. Suspending liquids selected from the group consisting of dibenzyl benzenes, diphenyl ether and mixtures thereof have been found to be especially useful, particularly when the molecules of the feedstock contain one carbon atom.

Although the present process may be conducted in the presence of a solid particles/liquid slurry, it is more preferred that step (a), and preferably step (b), be conducted with the solid particles present in the fluidized state. The use of fluidized solid particles provides improved flexibility in choosing various components, for example, the regeneration medium, relative to the slurry operation in which the suspending liquid may be sensitive to given components.

The chemical conversion or reaction obtained by practicing the present invention can vary widely and depends, for example, on the feedstock and catalyst employed and on the feedstock/catalyst contacting conditions used. Substantially any chemical conversion or reaction which is capable of being catalyzed by a small pore MCSC may be conducted while practicing the present invention. Examples of reactions which may be obtained include cracking; disproportionation; olefin production from non-olefin feedstocks; olefin interconversion; aldol, e.g., aldehyde-aldehyde, ketone-ketone, aldehyde-ketone and aldehyde or ketone-aromatic component, condensation; condensation reactions to produce cyclic lactams; isoprene formation; alkylation; and isomerization. One particularly preferred chemical conversion or reaction involves olefin production from non-olefin feedstocks, more preferably feedstocks comprising aliphatic hetero compounds.

Substantially any feedstock or combination of feedstocks may be employed in the present invention. Such feedstock, i.e., reactant component or components, may be gaseous, solid or liquid at ambient conditions, i.e., 20° C. and atmospheric pressure. The feedstock may be inorganic, organic or a combination of inorganic and organic components. The present reaction system is particularly applicable to organic feedstocks, preferably having molecules comprising carbon and hydrogen, and more preferably at least one other element. This other element is preferably selected from the group consisting of oxygen, sulfur, halogen, nitrogen, phosphorus and mixtures thereof, with oxygen being particularly preferred.

As alluded to previously, the present invention is particularly useful in converting feedstocks having relatively small molecules, i.e., molecules having relatively small kinetic diameters. Thus, the feedstock preferably contains 1 to about 10, more preferably 1 to about 4, carbon atoms per molecule. Aliphatic hetero compounds are particularly preferred feedstocks for use in the present invention, especially when light olefins, i.e., olefins containing 2 to about 6 and preferably 2 to 4 carbon atoms per molecule, are to be produced. When light olefins are the desired product, such olefins are preferably produced as the major hydrocarbon product, i.e., over 50 mole percent of the hydrocarbon product is light olefins. The term "aliphatic hetero compounds" is employed herein to include alcohols, halides, mercaptans, sulfides, amines, ethers and carbonyl compounds (aldehydes, ketones, carboxylic acids and the like). The aliphatic moiety preferably contains from 1 to about 10 carbon atoms and more preferably contains from 1 to about 4 carbon atoms. Suitable reactants include lower straight or branched chain alkanols, their unsaturated counterparts, and the nitrogen, halogen and sulfur analogue of such. Representative of suitable aliphatic hetero compounds include: methanol; methyl mercaptan, methyl sulfide; methyl amine; dimethyl ether; ethanol; ethyl mercaptan; ethyl chloride; diethyl ether; methyethyl ether; formaldehyde; dimethyl ketone; acetic acid; n-alkyl amines; n-alkyl halides and n-alkyl sulfides having n-alkyl group having 3 to 10 carbon atoms; and mixtures thereof. Components containing one carbon atom per molecule are especially attractive as feedstocks in the present process. In one embodiment, e.g., where light olefins are the desired products, the feedstock is preferably selected from the group consisting of methanol, ethanol, dimethyl ether, diethyl ether and mixtures thereof, with methanol being particularly preferred.

In certain instances, it is preferred that the feedstock/catalyst contacting conditions be such that the contacting temperature exceed the critical temperature of the feedstock. In other words, in certain embodiments, the feedstock is preferably in the supercritical state at the step (a) feedstock/catalyst contacting conditions. Having the feedstock in the supercritical state is particularly useful when the feedstock contains 1 to about 10, more preferably 1 to about 4, carbon atoms per molecule.

The product or products obtained from the step (a) feedstock/catalyst contacting will, of course, depend, for example, on the feedstock, catalyst and conditions employed. Preferably, the desired product is organic. However, it should be noted that a necessary, and therefore desired, reaction by-product may be inorganic even when the primary product sought is organic. This is exemplified by the conversion of methanol to light olefins plus water. The organic product or products have molecules which preferably include carbon and hydrogen. In one embodiment, the desired product preferably contains 1 to about 10, more preferably 1 to about 4, carbon atoms per molecule. The desired product or products preferably have kinetic diameters which allow such product or products to be removed from or escape from the pores of the CMSC.

In addition to the feedstock, a diluent may be used in conjunction with the feedstock if desired and/or beneficial to the overall process. Such diluent may be mixed or combined with the feedstock prior to the step (a) feedstock/catalyst contacting or it may be introduced into the reaction zone separately from the feedstock. Preferably, the feedstock and diluent are both substantially continuously fed to the reaction zone during step (a). Such diluent preferably acts to moderate the rate, and possibly also the extent, of feedstock chemical conversion and may also act to aid in temperature control.

Typical of the diluents which may be employed in the instant process are helium, argon, nitrogen, carbon monoxide, carbon dioxide, hydrogen, water, aliphatic hydrocarbons, aromatic hydrocarbons and mixtures thereof. When the feedstock contains 1 to about 4 carbon atoms per molecule, the diluent, if any, is preferably selected from the group consisting of helium, argon, nitrogen, carbon monoxide, carbon dioxide, hydrogen, water and mixtures thereof, with water, nitrogen and mixtures thereof, in particular water, being more preferred. The amount of diluent employed, if any, may vary over a wide range depending on the particular application involved. For example, the amount of diluent may be in an amount in the range of about 0.1% or less to about 99% or more of the moles of feedstock.

In one embodiment, the solid composition includes at least one added component effective to promote the action of the regeneration medium. For example, the catalyst may include at least one metal component effective to promote the oxidation of the carbonaceous deposit material. Of course, such metal component should have no substantial adverse effect on the desired chemical conversion. The specific added component depends on the requirement of the particular application involved. Examples of such added components include components of transition metals, such as nickel, cobalt, iron, manganese, copper and the like; the platinum group metals such as platinum, palladium, rhodium and the like; and the rare earth metals such as cerium, lanthanum and the like, and mixtures thereof. If an added metal component is used, it is preferred that this component be present as a minor amount, more preferably as about 1 ppm to about 20%, by weight (calculated as elemental metal) of the weight of catalyst, including the matrix materials, employed.

Alternately to the oxidative catalyst regeneration, a reducing medium can be employed in step (b) to regenerate the catalyst. Such reducing medium, preferably selected from the group consisting of hydrogen, carbon monoxide and mixtures thereof, and in particular hydrogen, can, for example, be used to react with molecules, e.g., of carbonaceous deposit material, on the solid composition to remove a portion of the carbonaceous deposit material from the solid composition. In one embodiment, the reducing medium is hydrogen and the catalyst includes at least one component, preferably a metal component, effective to promote hydrogenation and/or hydrocracking of molecules present on the solid composition at the conditions of the reductive regeneration of step (b).

Combinations of oxidative and reductive catalyst regeneration may be employed.

In between steps (a) and (b), the catalyst is preferably subjected to purging to minimize, preferably substantially eliminate contact between the feedstock/product of step (a) and the regeneration medium/regeneration medium product of step (b). The purge media employed should have no substantial adverse effect on the catalyst or on the desired chemical conversion or reaction, and are preferably substantially gaseous at the conditions at which the purging occurs. The amount and flowrate of these media employed may vary over a wide range provided that such amount and flowrate are effective to achieve the degree of purging desired. Excessive amounts and flowrates of purge media should be avoided to control purge time and cost. Of course, sufficient purge media should be employed to effectively eliminate any dangerous conditions in the system.

The purge media useful in the present invention may vary depending on the specific application involved. In certain embodiments, the purge media are preferably selected from the group consisting of water, nitrogen and mixtures thereof, in particular water.

The instant process may be carried out in a single reaction zone or a plurality of such zones arranged in series or in parallel. After the desired product or products are separated from the solid particles using, for example, solid/gas separation devices such as cyclone separators, various techniques, such as distillation, adsorption and the like, can be used to recover or purify such product or products. Steps (a) and (b) can be conducted in the same zone or can be conducted in separate zones with solid particles being transported between the zones.

The conditions at which step (a) occurs can vary widely depending, for example, on the specific feedstock and catalyst employed and on the specific product or products desired. The present process is particularly applicable with step (a) feedstock/catalyst contacting temperatures in excess of about 200° C., more preferably in excess of about 300° C., and with step (a) pressures in excess of about 10 psig., more preferably in excess of about 50 psig. If light olefins are to be produced from feedstock containing 1 to about 4 carbon atoms per molecule, step (a) temperatures are preferably in the range of about 200° C. to about 600° C. or even about 700° C., more preferably about 350° C. to about 550° C. and still more preferably about 400° to about 500° C., with step (a) pressures preferably below about 1500 psig. The residence time of the feedstock in the step (a) contacting zone may be selected depending, for example on the specific feedstock and catalyst employed, and on the specific product or products desired.

In the event that the feedstock includes 1 to about 4 carbon atoms per molecule and the product includes 1 to about 6 carbon atoms per molecule, in particular olefins containing 2 to about 4 carbon atoms per molecule, it is preferred that the conditions in step (a) be controlled to provide at least about 90%, more preferably at least about 95% and still more preferably substantially 100%, conversion of the feedstock, on a once-through basis. In one embodiment, the feedstock conversion can be monitored to control the amount of solid composition to be withdrawn from step (a) and subjected to step (b) or, if both step (a) and step (b) are to be conducted in a single vessel, when the solid composition is to be regenerated, i.e., when step (b) is to be performed. In turn, step (b) is preferably monitored and controlled so that the desired degree of carbonaceous deposit material removal is achieved. Thus, both steps (a) and (b) are preferably controlled so that the present process operates within a desired "window" of catalytic activity with the end result of providing effective processing, e.g., increased yields of desired product or products.

In one embodiment, when the feedstock comprises methanol and the product is selected from the group consisting of light olefins and mixtures thereof, the presence of dimethyl ether in the contacting zone effluent can be used to monitor the catalytic activity of the solid composition in the contacting zone. In such a system, preferably at least about 90%, more preferably at least about 95% and still more preferably substantially all, of the methanol in the feedstock is converted.

An increase in the amount of dimethyl ether in the contacting zone effluent can be used as an indication that one or more of the catalytic properties of the solid composition in the contacting zone can be improved by subjecting the solid composition to step (b). In one specific embodiment, the methanol/solid composition contacting is preferably terminated, and the solid composition is preferably subjected to step (b), at a time prior to the time when the relative amount of dimethyl ether in the contacting zone effluent is more than about 100%, more preferably more than about 50% and still more preferably more than about 20%, greater than the Initial Relative Amount of dimethyl ether. The step (a) methanol/solid composition contacting is preferably controlled so that the relative amount of dimethyl ether in the contacting zone is less than about 100%, more preferably less than about 50% and still more preferably less than about 20%, greater than the Initial Relative Amount of dimethyl ether.

As used herein, the term "relative amount of dimethyl ether" means the moles of dimethyl ether in the methanol/solid composition contacting zone effluent per mole of methanol fed to the contacting zone. The term "Initial Relative Amount of dimethyl ether" means the relative amount of dimethyl ether obtainable at the step (a) contacting conditions using the solid composition present during the initial portion of the step (a) contacting or 0.5% of the moles of methanol converted during the initial portion of the step (a) contacting, whichever is greater.

The following non-limiting examples are provided to better illustrate the invention.

EXAMPLES 1 TO 12

A number of experiments were conducted to demonstrate the effect of catalyst activity level on chemical conversion using small pore molecular sieve catalysts.

The apparatus used in these experiments involved a ⅜ inch O.D. titanium U-tube reactor which was filled with 36 grams of one-sixteenth inch diameter extrudates, diluted with 36 grams of quartz chips. The extrudates included about 80% by weight of SAPO-34 and about 20% by weight of silica binder, and were prepared using a conventional catalyst extrusion technique. The reactor temperature was controlled by a fluidized bed heater in which it was located. Pure methanol was fed to the reactor using a 150 rpm FMI metering pump with a model RHOCKC microhead. The methanol was vaporized and preheated in a section of steam jacketed one-inch pipe before entering the reactor. Methanol flow was measured by periodically timing the level change in a burette on the pump suction line. A small rotameter was also used to check methanol flows.

Nitrogen diluent was fed from high-pressure cylinders. It was electrically preheated before mixing with the methanol upstream of the preheater, to help vaporize the methanol. Nitrogen flow was controlled with a Veriflow flow controller, and measured with a 1A-15-1 rotameter.

Pressure in the reactor was controlled with a Grove pressure regulator on the reactor outlet. Pressure was dropped after the reactor outlet to about 5 psig, to avoid condensation in the sample lines. From the reactor, steam-jacketed lines led to the gas chromatograph, then to the two integral orifice blocks used for measuring gas flows. Fittings and other potentially cool areas were electrically heated using heavy duty heat tapes and insulated to prevent any condensation of water or heavy products in the sample lines. The gas stream then went to a condenser and knock-out pot, through a wet test meter, and was vented back to a hood.

Regeneration was controlled by a set of low wattage ASCO solenoid switching valves, controlled by a Xanadu timer. At the beginning of a regeneration cycle the methanol feed was switched away from the reactor and through a recycle line back to the feed tank; simultaneously, a nitrogen purge was switched on to the reactor. After 20 minutes of purging, regeneration air was switched on, and the catalyst was regenerated for 140 minutes. The reactor was then purged with nitrogen again for 20 minutes before starting the methanol flow again and beginning another run. Regeneration temperature was also controlled via the timer: it "ramped" up to 500° C. during the early part of the regeneration cycle, and the main part of the regeneration cycle the temperature was "ramped" back down to the starting temperature for the next run. Thus, all regenerations were conducted at 500° C.

The product gas was analyzed with a Varian 3700 gas chromatograph, containing two columns (Carbosieve S and Porapack R) with thermal conductivity and flame ionization detectors respectively.

The initial sampling time of the GC was controlled by the Xanadu timer, although the time between samples was controlled by one of the CDS-111 integrators. The column switching which was necessary to obtain the simultaneous TCD and FID analyses was also controlled by the integrator in conjunction with a Varian external events module. Thus, all samples were taken at the same times into the runs.

The products were samples at times into the run of 10, 40, 70, 100, 130 and 160 minutes.

Examples 1 to 12 were conducted at the following reaction conditions:

| WHSV, hr$^{-1}$ | 1.5 |
|---|---|
| Pressure, psig | 60 |
| N$_2$ Dilution, mole % | 80 |

The reaction temperature during Examples 1 to 6 was maintained at about 375° C., while the reaction temperature during Examples 7 to 12 was maintained at about 475° C.

Results from these Examples are shown in Table I.

TABLE I

| EX. | TIME MIN. | CH$_3$OH CONV. % | dme[1] | CARBON SELECTIVITY[2] | | | | | | |
|---|---|---|---|---|---|---|---|---|---|---|
| | | | | CH$_4$ | C$_2$H$_4$ | C$_2$H$_6$ | C$_3$H$_6$ | C$_3$H$_8$ | C$_4$ | C$_5$ |
| 1 | 10 | 100.00 | 0.00 | 0.82 | 6.04 | 2.06 | 15.43 | 44.44 | 27.43 | 3.77 |
| 2 | 40 | 100.00 | 0.00 | 0.52 | 15.46 | 1.60 | 43.62 | 10.61 | 26.38 | 1.75 |
| 3 | 70 | 99.70 | 0.26 | 0.47 | 24.16 | 1.37 | 52.06 | 3.60 | 16.62 | 1.71 |
| 4 | 100 | 97.70 | 2.22 | 0.51 | 30.39 | 1.14 | 51.54 | 1.88 | 13.42 | 1.14 |
| 5 | 130 | 82.70 | 17.10 | 0.50 | 31.45 | 0.82 | 50.60 | 1.41 | 14.06 | 1.17 |
| 6 | 160 | 74.40 | 23.12 | 0.88 | 33.58 | 1.03 | 46.83 | 1.77 | 14.43 | 1.47 |
| 7 | 10 | 99.90 | 0.00 | 2.75 | 18.46 | 4.32 | 29.60 | 24.45 | 16.49 | 3.93 |
| 8 | 40 | 100.00 | 0.00 | 3.15 | 34.36 | 2.25 | 41.60 | 3.76 | 12.44 | 2.16 |
| 9 | 70 | 97.50 | 2.38 | 4.01 | 46.65 | 1.22 | 37.01 | 0.92 | 7.85 | 1.31 |
| 10 | 100 | 30.10 | 53.00 | 9.36 | 42.54 | 1.07 | 32.91 | 0.80 | 10.17 | 2.01 |
| 11 | 130 | 13.80 | 67.15 | 13.81 | 31.90 | 1.23 | 27.61 | 0.01 | 12.27 | 1.53 |
| 12 | 160 | 10.40 | 70.21 | 15.27 | 28.14 | 1.61 | 25.32 | 1.21 | 12.86 | 2.01 |

[1] % of Methanol forming Dimethyl Ether
[2] % of carbon atoms in the total listed products present in the given product.

As the Examples proceed from 1 to 6 and from 7 to 12, the catalyst is deactivated by the formation of carbonaceous deposit material. The results shown in Table I indicated that propane production is reduced as the catalyst becomes deactivated. Maximum ethylene and propylene production is achieved using a partially deactivated catalyst. Thus, if ethylene and/or propylene are desired products, a window of catalyst activity can be utilized to achieve improved yields of these materials. In order to operate within this window of catalyst activity, the catalyst is partially regenerated so that the feedstock contacts a partially deactivated catalyst. The effect on product selectivity caused by deactivation is particularly surprising when, as in the present invention, small pore CMSCs are used.

Without wishing to limit the present invention to any theory or mechanism of operation, one possible explanation is that the carbonaceous deposit material, at least at the early stages of the feedstock/solid particles contacting, acts to deactivate the binder material which promotes the undesired or non-selective reactions. Also, relatively large, possibly aromatic molecules may form in the pores of the catalyst and become trapped. Once this has occurred, no more large molecules can form and the desired reaction, e.g., light olefin production, is free to take place. The catalyst requires partial regeneration to remove a portion of the carbonaceous deposit material so that an acceptable level of feedstock conversion is achieved or maintained. During the partial regeneration, at least a portion of the molecules trapped in the catalyst survive to improve the effectiveness, e.g., selectivity of the catalyst.

EXAMPLE 13

A commercially sized fluidized bed reaction system is constructed to produce 5000 barrels per day of mixed ethylene and propylene from methanol. The system includes three reactor vessels in parallel. Each of the reactor vessels are equipped with a number of cyclone separators to aid in removing gases from the reactor vessel while holding the catalyst inside. The system also includes a conventional product handling/separation sub-system to recover and purify the products to the extent desired.

The feed system to each of the reactor vessels includes a separate steam inlet. Steam is substantially continuously fed to each of the vessels. A valved methanol inlet and a valved air inlet are also provided to each of the vessels. The methanol and air inlets are controlled so that only one of methanol or air is fed to any one reactor vessel at any one time.

Each of these reactor vessels are operated on the following reaction/regeneration cycle. Solid particles, similar in composition to that prepared in Example 1, is placed in the reaction vessel and heated to a temperature of 500° C. Vaporized and heated methanol is fed to the vessel (along with the steam diluent) to produce light olefins which are removed from the vessel through the cyclone separators. Substantially all of the methanol is converted. Throughout the cycle the catalyst is maintained at a temperature of about 500° C. and a pressure of about 80 psig. After a period of time, methanol flow is stopped and steam purges the vessel of methanol. After the purge, a limited amount of air is introduced into the reactor vessel to remove about 50% of the carbonaceous deposit material on the solid particles. This air/solid particles contacting is carried out so that the rate of carbonaceous deposit material removal is reduced relative to such removal rate when substantially all of the carbonaceous deposit material is to be removed from the solid particles. After the desired carbonaceous deposit material removal,, the flow of air is stopped and steam purges the vessel of air. The solid particles include about 5% by weight of carbonaceous deposit material. At this point, the cycle is begun again. The time sequencing of this cyclic operation is such that no less than two of the reactor vessels operate in the reaction mode at any one time.

This cyclic operation is effective in producing ethylene and propylene, in particular ethylene, from methanol.

While the present invention has been described with respect to various specific examples and embodiments, it is to be understood that the invention is not limited thereto and that it can be variously practiced within the scope of the following claims.

What is claimed is:

1. A process for catalytically converting a feedstock containing one or more compounds selected from the group consisting of alcohols, halides, mercaptans, sulfides, amines, ethers, and carboxyl compounds, said compounds having from 1 to about 4 carbon atoms per molecule, into a product containing light olefins which comprises:
    (a) contacting said feedstock with a crystalline microporous three dimensional solid catalyst comprising a silicoaluminophosphate molecular sieve having pores with diameters of less than 5 Angstroms, said contacting being at conditions effective to convert said feedstock into said product and to form carbonaceous deposit material on said solid catalyst;
    (b) contacting said carbonaceous deposit material-containing solid catalyst with regeneration medium at conditions effective to remove only a portion of said carbonaceous deposit material from said solid catalyst to form a partially regenerated solid catalyst having from about 2% to about 30% by weight of said carbonaceous deposit material and providing improved selectivity to said product relative to said solid catalyst containing less carbonaceous deposit material; and
    (c) repeating step (a) using as said solid catalyst in step (a) at least a portion of said solid catalyst previously subjected to step (b).

2. The process of claim 1 wherein said partially regenerated solid catalyst contains about 4% to about 20% by weight of carbonaceous deposit material.

3. The process of claim 1 wherein said feedstock is selected from the group consisting of methanol, ethanol, dimethyl ether, diethyl ether and mixtures thereof.

4. A process for catalytically converting a feedstock consisting essentially of methanol into a product containing ethylene, propylene, butylene and mixtures thereof which comprises:
    (a) contacting said feedstock with a crystalline microporous three dimensional catalyst comprising a silicoaluminophosphate molecular sieve having pores with diameters of less than 5 Angstroms at conditions effective to convert said feedstock into said product and to form carbonaceous deposit material on said catalyst;
    (b) contacting said carbonaceous deposit material-containing catalyst with regeneration medium at conditions effective to remove only a portion of said carbonaceous deposit material from said catalyst to form a partially regenerated catalyst, said partially regenerated catalyst having from about 2% to about 30% by weight of said carbonaceous deposit material and providing improved selectivity to said product relative to said catalyst containing less carbonaceous deposit material; and
    (c) repeating step (a) using as said catalyst in step (a) at least a portion of said catalyst previously subjected to step (b).

5. The process of claim 4 wherein said catalyst is in the form of solid particles having a diameter from about 1 to 500 microns.

6. The process of claim 5 wherein step (a) takes place with said solid particles being in the fluidized state.

7. The process of claim 6 wherein step (b) takes place with said carbonaceous deposit material-containing solid particles being in the fluidized state.

8. The process of claim 5 wherein step (a) and step (b) occur in separate zones and said solid particles are transported between said zones.

9. The process of claim 8 wherein step (a) and step (b) occur in the same zone.

10. The process of claim 4 wherein said regeneration medium is a reducing medium or an oxidizing medium.

11. The process of claim 4 wherein said regeneration medium is an oxygen-containing gaseous medium.

12. The process of claim 12 wherein said reducing medium is selected from the group consisting of hydrogen, carbon monoxide and mixtures thereof.

13. The process of claim 4 wherein said catalyst includes at least one added component effective to promote the removal of said carbonaceous deposit material during step (b).

14. The process of claim 15 wherein said added component is a metal component.

15. The process of claim 4 wherein said catalyst comprises SAPO-34.

16. The process of claim 4 wherein said partially regenerated catalyst contains about 4% to about 20% by weight of carbonaceous deposit material.

* * * * *